(12) United States Patent
Nolen et al.

(10) Patent No.: US 6,660,775 B2
(45) Date of Patent: Dec. 9, 2003

(54) METHOD AND COMPOSITIONS FOR INHIBITING THE SCENT TRACKING ABILITY OF BITING MIDGES

(75) Inventors: James A. Nolen, West Greenwich, RI (US); Robert H. Bedoukian, West Redding, CT (US); Robert E. Maloney, Bethel, CT (US); Daniel L. Kline, Gainesville, FL (US)

(73) Assignees: BioSensory, Inc., Willimantic, CT (US); Bedoukian Research, Inc., Danbury, CT (US); The United States of America as represented by the Secretary of Agriculture, Washington, DC (US)

( * ) Notice: Subject to any disclaimer, the term of this patent is extended or adjusted under 35 U.S.C. 154(b) by 74 days.

(21) Appl. No.: 10/078,869

(22) Filed: Feb. 19, 2002

(65) Prior Publication Data

US 2003/0158267 A1 Aug. 21, 2003

(51) Int. Cl.$^7$ .................. A01N 31/00; A01N 25/02; A01N 25/04; A01N 25/06
(52) U.S. Cl. .................. 514/739; 514/772; 514/782; 514/785; 514/786; 514/919; 424/405; 424/DIG. 10
(58) Field of Search .................. 514/739, 772, 514/782, 785, 786, 919; 424/405, DIG. 10

(56) References Cited

U.S. PATENT DOCUMENTS

| | | | | |
|---|---|---|---|---|
| 5,633,236 A | * | 5/1997 | Warren et al. | 514/63 |
| 5,721,274 A | | 2/1998 | Vander Meer et al. | 514/531 |
| 5,799,436 A | * | 9/1998 | Nolen et al. | 43/112 |
| 6,267,953 B1 | * | 7/2001 | Bernier et al. | 424/84 |

FOREIGN PATENT DOCUMENTS

WO 00/38512 * 7/2000

OTHER PUBLICATIONS

CABA abstract, accession No. 82:23308 (1981).*
Chemical Abstracts 118 : 98513 (1992).*
W.V. King, "Chemicals Evaluated as Insecticides and Repellents at Orlando, Fla.";Agricultural Handbook No. 69, pp. 1–17, 218 and 246, May 1954.
D.J. Burton "'Intrinsic mosquito repellency values of some chemical compounds'" American Perfumer and Cosmetics, pp. 41–44, Apr. 1969.

* cited by examiner

*Primary Examiner*—John Pak
(74) *Attorney, Agent, or Firm*—Ohlandt, Greeley, Ruggiero & Perle, LLP; George W. Rauchfuss, Jr.

(57) ABSTRACT

The ability of biting midges to locate a target by olfactory emissions of the target is inhibited by dispensing into a spatial area an inhibiting effective amount of at least one inhibiting compound selected from the group consisting of 3-methyl-1-alkene-3-ols of the formula:

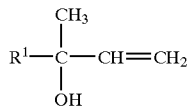

and 3-methyl-1-alkyn-3-ols of the formula:

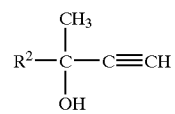

wherein $R^1$ and $R^2$ are each independently a saturated or unsaturated aliphatic hydrocarbon group containing from 1 to about 12 carbon atoms.

19 Claims, No Drawings

METHOD AND COMPOSITIONS FOR INHIBITING THE SCENT TRACKING ABILITY OF BITING MIDGES

FIELD OF THE INVENTION

This invention relates to a method and compositions for inhibiting the ability of biting midges to locate or track a target, such as an animal or human body, by scent detection. More particularly, the invention relates to the use of certain compounds in compositions to inhibit biting midges' ability to detect a target by scent detection.

BACKGROUND

As anyone that has significant outdoor experience can attest, biting midges can be terribly annoying and amount to a significant problem. Their bites can produce burning and itching welts. Biting midges can have a significant economic impact since their presence often significantly discourages tourism in certain regions, particularly coastal regions where they may occur in large numbers.

These minute biting insects are also known commonly as "sandflies", "no-see-ums, "hequenes" in Mexico and "punkies" in Great Britain. Biting midges are particularly abundant in areas where there are mangrove swamps or salt marshes. In the United States they are particularly abundant in coastal Florida and North Carolina. Midges belong to the insect order Diptera (2-winged flies), family Ceratopogonidae, genus Leptoconops and Culicoides. It is only the female of this species that bites and takes blood, and the time of greatest biting activity is generally around dawn or dusk.

Of the many species of biting midges of the genus Cucicoides, at least about 111 species, certain prevalent species, such as *Culicoides furens* and *Culicoides barbosai* species, are known to be vectors of a human nematode parasite, *Mansonella ozzardi*. This worm lives primarily in the blood and female midges ingest the microfilariae (juvenile forms) when they take blood and then transmit the parasite to uninfected persons. The species *Leptoconops becquaerti*, of the genus Leptconops prevalent in Costa Rica, is known to transmit a filarial worm in humans called *Dipeialoneina ozzardi. Culicoides arabae, Culicoides foxi* and *Culicoides barbosai* have been collected from horses and mules and *Culicoides insignis* collected from cattle and are a problem for these animals.

Compounds, compositions and formulations for protecting human beings from being bitten by biting midges are known in the art. Generally, these compounds, compositions and formulations are based on their ability to persist on the skin of the person upon topical or surface application for a time sufficient to repel biting midges. Numerous adjuvant materials have been added to biting midge repellents to increase the persistence of the repellents to the skin of a person. Additionally, low volume spraying of chemical insecticides has been employed, but not with great success. Moreover, spraying of such insecticidal chemicals is environmentally and from a health-wise standpoint undesirable. However, despite the various attempts to improve the repelling activity of the known biting midge repellents, these attempts have generally not been successful, as almost anyone who has used such biting midge repellents can attest.

Thus, the art has been searching for new and more effective repellents against biting midges. However, the search for more effective biting midge repellents has not generally been met with success since most biting midge repellents have been found only to possess a limited degree of repellency and are generally not particularly effective. There is, therefore, a need for more effective means to deter biting midges from locating and biting humans and other targets such as birds and livestock. from locating and biting humans and other targets such as birds and livestock. Moreover, this need has recently become more acute and urgent because biting midges have been discovered to be carriers of significant diseases that can be passed on to a target by the biting midges biting the target. A further need is to be able to reduce or eliminate the need to use environmentally unfriendly pesticides.

SUMMARY OF THE INVENTION

The inventors have discovered that compounds, compositions and formulations heretofore proposed as repellents for biting midges have lacked the necessary efficacy due to the ability of biting midges to locate and be drawn to the targets by olfactory emissions of the target. Thus, if a biting midge enters a zone or space where a potential target is located, the biting midge can be attracted to the target by olfactory emissions of the target and, this olfactory attraction is sufficient to overcome any repellency activity of the repellent compound, composition or formulation applied on the target. Therefore, the present invention provides compositions and formulations containing compounds usable in methods and apparatus for inhibiting the olfactory target tracking abilities of biting midges when an effective amount of the inhibiting compound(s) is/are dispersed in a three dimensional atmospheric space.

According to this invention, the ability of biting midges to locate a target is inhibited by dispensing into a spatial area an inhibiting effective amount of at least one inhibiting compound selected from the group consisting of 3-methyl-1-alkene-3-ols of the formula:

$$R^1-\underset{\underset{OH}{|}}{\overset{\overset{CH_3}{|}}{C}}-CH=CH_2$$

and 3-methyl-1-alkyn-3-ols of the formula:

$$R^2-\underset{\underset{OH}{|}}{\overset{\overset{CH_3}{|}}{C}}-C\equiv CH$$

wherein $R^1$ and $R^2$ are each independently a saturated or unsaturated aliphatic hydrocarbon group containing from 1 to about 12 carbon atoms.

The inhibiting compound can be dispensed into the three dimensional atmospheric space by any suitable means sufficient to provide an inhibiting effective amount of the inhibiting compound(s). Such dispensing means includes, for example, evaporation, atomization and ionic dispersion of the inhibiting compound from any suitable composition or formulation. Such composition or formulation will generally comprise a base vehicle containing at least one of the inhibiting compounds.

DETAILED SUMMARY OF THE INVENTION

The inventors have discovered that if an effective amount of at least one inhibiting compound selected from the group consisting of 3-methyl-1-alkene-3-ols of the formula:

$$R^1-\underset{\underset{OH}{|}}{\overset{\overset{CH_3}{|}}{C}}-CH=CH_2$$

and 3-methyl-1-alkyn-3-ols of the formula:

$$R^2-\underset{\underset{OH}{|}}{\overset{\overset{CH_3}{|}}{C}}-C\equiv CH$$

wherein $R^1$ and $R^2$ are each independently a saturated or unsaturated aliphatic hydrocarbon group containing from 1 to about 12 carbon atoms is dispensed into the atmosphere of a three dimensional environmental space, the ability of biting midges to locate and track a target, such as humans, birds or livestock, by the target's olfactory emissions is inhibited.

Any suitable 3-methyl-1-alkene-3-ols or 3-methyl-1-alkyn-3-ol of the formulas may be employed in the method, compositions and apparatus of this invention. Especially suitable inhibiting compounds are nerolidol, 3-methyl-1-octen-3-ol, linalool and dehydrolinalool. Depending on the particular biting midge species, either the 3-methyl-1-alkyn-3-ols or the 3-methyl-1-alkene-3-ols are better inhibitors than the other class of components and will be preferred for that species of biting midge. The inhibiting compounds may be utilized singly or as mixtures of two or more of such compounds.

Any suitable inhibiting effective amount of the inhibiting compound(s) may be employed. Such inhibiting effective amounts can include amounts, based on the square footage of land or base surface area of the environmental area to be treated, within the range of from about 0.000005 g/hr/ft$^2$ to about 0.004 g/hr/ft$^2$, preferably amounts within the range of from about 0.00015 g/hr/ft$^2$ to about 0.0002 g/hr/ft$^2$, and especially an amount of about 0.00016 g/hr/ft$^2$.

The inhibiting compounds for use in this invention may be provided in an essentially pure form of the inhibiting compounds or as a component of a natural essential oil having a concentration of an inhibiting compound sufficient to make it practical and feasible to dispense an inhibiting effective amount of inhibiting compound. Generally, the essential oil will contain a concentration of the inhibiting compound of at least about 1%, preferably at least about 5%, and especially at least about 50% by weight. For example, the inhibiting compound can be provided as a synthetically produced, essentially pure compound or as a component of an essential oil such as basil oil, ho wood oil and the like.

The inhibiting compounds of this invention, or essential oils containing such inhibiting compounds, may be employed in any formulation suitable for dispensing inhibiting effective amounts of the compounds. The compounds will generally be employed in formulations comprising a suitable vehicle containing the inhibiting compounds. For example, the inhibiting compound can be formulated in a specially formulated wax-like medium or vehicle engineered to release desired amounts of vaporous inhibiting compound at ambient temperatures, such as those mediums or vehicles available from Koster Keunen of Watertown, Conn. An example of such a wax-like medium available from Koster Keunen is known as Insect Repellent Wax Bar No. 9, which is a blend of waxes having the following general composition: fatty acids ranging in carbon chain length of from $C_{16}$ to $C_{22}$, fatty alcohols ranging in carbon chain length of from $C_{16}$ to $C_{22}$, paraffinic hydrocarbons ranging in carbon chain length of from $C_{19}$ to $C_{47}$, branched hydrocarbons ranging in carbon chain length of from $C_{23}$ to $C_{69}$, beeswax and other natural waxes such as candelilla and carnauba. The wax mixture will generally be formulated with concentrations of the inhibiting compounds of this invention ranging from about 20% to 60% and the formulation has a congealing point which may vary from about 75° C. to about 45° C. Alternatively, the inhibiting compound can be formulated in a porous medium or vehicle suitable for releasing effective amounts of the inhibiting compound. As an example of such porous medium or vehicle is a polyester membrane material having micropores encasing a block of inhibiting compound saturated fibers that gradually releases the inhibiting compound so that it permeates the microporous membrane and is released to the environment. Such porous membrane known as World of Fragrance™ cups is available from Waterbury Companies, Inc. of Waterbury, Conn.

The formulations can be placed in any suitable container or device for dispensing the inhibiting compound. For example, the formulations can be placed in a suitable fan-equipped device so that one can obtain, for example, fan-driven evaporation of the inhibiting compound from a porous medium or wax-like medium containing the inhibiting compound. As examples of such fan-equipped devices, there can be mentioned the devices disclosed in U.S. Pat. No. 5,370,829 of Waterbury Companies, Inc. and the apparatus disclosed in U.S. Pat. No. 5,799,436 of BioSensory Insect Control Corporation, each of said patents being incorporated herein by reference thereto.

Another suitable means of dispensing the inhibiting compound is by atomization and/or ionic dispersion of the compound as suitable-sized, positively-charged droplets from a suitable atomization or ionic dispersing apparatus, such as the Ionic Wind™ device, available from Brandenburg, Ltd. of Brierery Hill, United Kingdom.

The inhibiting compounds of this invention are effective against any biting midges, such as for example, *Culicoides furens, Culicoides mississippiensis, Culicoides hollensis, Culicoidesbarbosai, Culicoides melleus, Culicoidesparaensis, Culicoides phlebotomus, Culicoides pseudodiabolicus, Culicoidesarabae, Culicoides foxi, Culicoides insignis, Culicoides insignids, Culicoidespusillus, Culicoides filarifer, Culicoides alaskensis, Culicoides edeni, Culicoides furensoides, Leptoconops becquaerti* and the like.

The use of this invention is illustrated by the following non-limited examples.

EXAMPLE 1

A device comprising a cylindrical housing essentially shaped like an opened one-gallon paint can, was equipped to release determinable amounts of one or more of $CO_2$, octenol and test compound of this invention. The device housing was equipped (covered) at it its open end with an electrical grid operating at a temperature of approximately 110° F. (44° C.) for killing any midges attracted to the grid and thereby collecting the killed midges in the housing. With the device in operation, biting midges would be attracted by the scent of $CO_2$ and/or octenol eminating from the interior of the housing and from the heat of the electrical grid. Then, with the additional introduction of test compound from the housing it was possible to determine the inhibiting effect of the test compound by determining the decrease in biting midges attracted and killed by the teat device. The test was conducted in a designated test area known for its abundance of biting midges along the Indian River in Vero Beach, Fla. at the U.S. Department of Agriculture test facility.

Competitive tests were conducted over a twelve day period in September. During Days 1 to 3 and 7 to 9 the test conditions of the test device were set to mimic a bird as the target, namely the device emitted 50 cc/min $CO_2$ and no octenol, and during Days 4 to 6 and 10 to 12 the test conditions were set to mimic a mammal as the target, namely the device emitted 50 cc/min $CO_2$ and 7 mg/hr octenol. In these competitive tests, the inhibiting compound was either not emitted (Days 1 to 6) or emitted (Days 7 to 12). The test then determined the number of midges killed and collected in the device without the test compound present, and the number of midges killed and collected in the device with the test compound present in order to determine the ability of the test compound to inibit the ability of the biting midges (*Culicoides furens*) to sense the mimiced target.

Test conditions and results of the competitive tests are set forth in the following Table 1.

TABLE 1

| Day | $CO_2$ cc/min | Octenol mg/hr | Linalool mg/hr | Midges collected |
|---|---|---|---|---|
| 1 | 50 | 0 | 0 | 103 |
| 2 | 50 | 0 | 0 | 5 |
| 3 | 50 | 0 | 0 | 68 |
| 1–3 | | | | Total 176 |
| 1–3 | | | | Avg./day 59 |
| 7 | 50 | 0 | 1 | 13 |
| 8 | 50 | 0 | 1 | 5 |
| 9 | 50 | 0 | 1 | 14 |
| 7–9 | | | | Total 32 |
| 7–9 | | | | Avg./day 11 |
| 4 | 50 | 7 | 0 | 338 |
| 5 | 50 | 7 | 0 | 1242 |
| 6 | 50 | 7 | 0 | 1830 |
| 4–6 | | | | Total 3410 |
| 4–6 | | | | Avg./day 1137 |
| 10 | 50 | 7 | 1 | 29 |
| 11 | 50 | 7 | 1 | 81 |
| 12 | 50 | 7 | 1 | 364 |
| 10–12 | | | | Total 474 |
| 10–12 | | | | Avg./day 158 |

Linalool reduced the average biting midge kill counts by 81% (from 59 to 11) over the three trials for the device mimicing a bird and by 86% over the three trial for the device mimicing a mammal evidencing the ability of linalool to inhibit the ability of biting midges to sense the target when linaloolis present in the environment.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method of inhibiting the ability of biting midges to sense a target by olfactory sensing of the target within a three dimensional environmental space having a land or base surface area, the method comprising dispensing into the atmosphere of the three dimensional environmental space where biting midges are present in or expected to be near said space an inhibiting effective amount of at least one inhibiting compound selected from the group consisting of 3-methyl-1-alkene-3-ols of the formula:

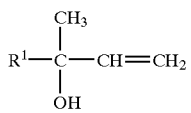

and 3-methyl-1-alkyn-3-ols of the formula:

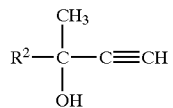

wherein $R^1$ and $R^2$ are each independently a saturated or unsaturated aliphatic hydrocarbon group containing from 1 to about 12 carbon atoms.

2. The method according to claim 1, wherein the inhibiting effective amount ranges from about 0.000005 g/hr/ft² to about 0.0004 g/hr/ft² based on the square footage of the land or base surface area of the environmental space.

3. The method according to claim 1, wherein the inhibiting effective amount ranges from about 0.00015 g/hr/ft² to about 0.0002 g/hr/ft² based on the square footage of the land or base surface area of the environmental space.

4. The method according to claim 1, wherein the at least one inhibiting compound is selected from the group consisting of nerolidol, 3-methyl-1-octen-3-ol, linalool and dehydrolinalool.

5. The method according to claim 1, wherein the at least one inhibiting compound comprises linalool.

6. The method according to claim 1, wherein the at least one inhibiting compound comprises dehydrolinalool.

7. The method according to claim 1, wherein the dispensing of the at least one inhibiting compound comprises dispensing by a method selected from the group consisting of volatilization, evaporation, atomization and ionic dispersion of the at least one inhibiting compound from a formulation comprising a vehicle containing the at least one inhibiting compound.

8. The method according to claim 7, wherein the dispensing comprises fan-driven evaporation of the at least one inhibiting compound from a formulation in which the vehicle is a porous medium.

9. The method according to claim 7, wherein the dispensing comprises fan-driven evaporation of the at least one inhibiting compound from a formulation in which the vehicle is a waxy solution.

10. The method according to claim 7, wherein the dispensing comprises atomization of the at least one inhibiting compound from the formulation.

11. The method according to claim 7, wherein the dispensing comprises ionic dispersion of the at least one inhibiting compound from the formulation.

12. The method according to claim 5, wherein the linalool is dispensed by fan-driven evaporation of linalool from a formulation of a porous medium containing linalool.

13. The method according to claim 5, wherein the linalool is dispensed by fan-driven evaporation of linalool from a formulation of a waxy solution containing linalool.

14. The method according to claim 5, wherein the linalool is dispensed by atomization of linalool from a formulation of a vehicle and linalool.

15. The method according to claim 5, wherein the linalool is dispersed by ionic dispersion of linalool from a formulation of a vehicle and linalool.

16. The method according to claim 6, wherein the dehydrolinalool is dispensed by fan-driven evaporation of dehydrolinalool from a formulation of a porous medium containing dehydrolinalool.

17. The method according to claim 6, wherein the dehydrolinalool is dispensed by fan-driven evaporation of dehydrolinalool from a formulation of a waxy solution containing dehydrolinalool.

18. The method according to claim 6, wherein the dehydrolinalool is dispensed by atomization of dehydrolinalool from a base composition.

19. The method according to claim 6, wherein the dehydrolinalool is dispersed by ionic dispersion of dehydrolinalool from a formulation of a vehicle and dehydrolinalool.

* * * * *